(12) United States Patent
Biedermann et al.

(10) Patent No.: US 8,784,491 B2
(45) Date of Patent: Jul. 22, 2014

(54) IMPLANT FOR STABILIZING VERTEBRAE OR BONES

(75) Inventors: Lutz Biedermann, VS-Villingen (DE);
Wilfried Matthis, Weisweil (DE);
Jürgen Harms, Karlsruhe (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 1232 days.

(21) Appl. No.: 12/343,232

(22) Filed: Dec. 23, 2008

(65) Prior Publication Data

US 2009/0204216 A1    Aug. 13, 2009

(30) Foreign Application Priority Data

Dec. 28, 2007  (EP) ..................................... 07025214

(51) Int. Cl.
*A61F 2/44* (2006.01)
*A61B 17/74* (2006.01)
*A61B 17/88* (2006.01)
*A61B 17/00* (2006.01)
*A61B 19/00* (2006.01)
*A61B 17/72* (2006.01)

(52) U.S. Cl.
CPC ... *A61B 17/8858* (2013.01); *A61B 2017/00526* (2013.01); *A61B 2017/00867* (2013.01); *A61B 17/744* (2013.01); *A61B 2019/306* (2013.01); *A61B 17/7258* (2013.01); *A61B 2019/304* (2013.01); *A61B 2017/0042* (2013.01)
USPC ....................................... 623/17.11; 606/270

(58) Field of Classification Search
USPC ........................................ 623/17.11; 606/270
See application file for complete search history.

(56) References Cited

U.S. PATENT DOCUMENTS

| | | |
|---|---|---|
| 5,059,193 A | 10/1991 | Kuslich |
| 5,390,683 A | 2/1995 | Pisharodi |
| 6,127,597 A | 10/2000 | Beyar et al. |

(Continued)

FOREIGN PATENT DOCUMENTS

| | | |
|---|---|---|
| JP | 2004-202226 A | 7/2004 |
| WO | WO 2004/110292 A2 | 12/2004 |

(Continued)

OTHER PUBLICATIONS

European Search Report for European Application No. 07025214.3, filed Dec. 28, 2007 in the name of Biedermann Motech GmbH, European Search Report dated Jun. 25, 2008 and mailed Jul. 3, 2008 (11 pgs.).

*Primary Examiner* — Thomas J Sweet
*Assistant Examiner* — Matthew Schall
(74) *Attorney, Agent, or Firm* — Christie, Parker & Hale, LLP

(57) ABSTRACT

An implant for use in stabilizing vertebral bodies or bones includes a first end and a second end, a tubular section between the first end and the second end having a longitudinal axis. The tubular section is flexible in such a way that it is expandable in a radial direction when a force acts in an axial direction which reduces the distance between the first end and the second end.

28 Claims, 8 Drawing Sheets

(56) References Cited

U.S. PATENT DOCUMENTS

| | | |
|---|---|---|
| 2002/0068939 A1 | 6/2002 | Levy et al. |
| 2003/0078581 A1 | 4/2003 | Frei et al. |
| 2003/0088249 A1 | 5/2003 | Furderer |
| 2003/0149431 A1* | 8/2003 | Varieur .................. 606/61 |
| 2004/0147929 A1 | 7/2004 | Biedermann et al. |
| 2006/0100706 A1 | 5/2006 | Shadduck et al. |
| 2007/0016200 A1 | 1/2007 | Jackson |
| 2007/0173826 A1 | 7/2007 | Canaveral et al. |
| 2007/0173939 A1* | 7/2007 | Kim et al. ............. 623/17.11 |

FOREIGN PATENT DOCUMENTS

| | | |
|---|---|---|
| WO | WO 2004/110300 A2 | 12/2004 |
| WO | WO 2005/048856 A1 | 6/2005 |
| WO | WO 2005/096975 A2 | 10/2005 |
| WO | WO 2007/028140 A2 | 3/2007 |
| WO | WO 2007/046691 A1 | 4/2007 |
| WO | WO 2007/078692 A2 | 7/2007 |
| WO | WO 2007/084427 A2 | 7/2007 |
| WO | WO 2007/124253 A2 | 11/2007 |
| WO | WO 2007/131002 A2 | 11/2007 |

* cited by examiner

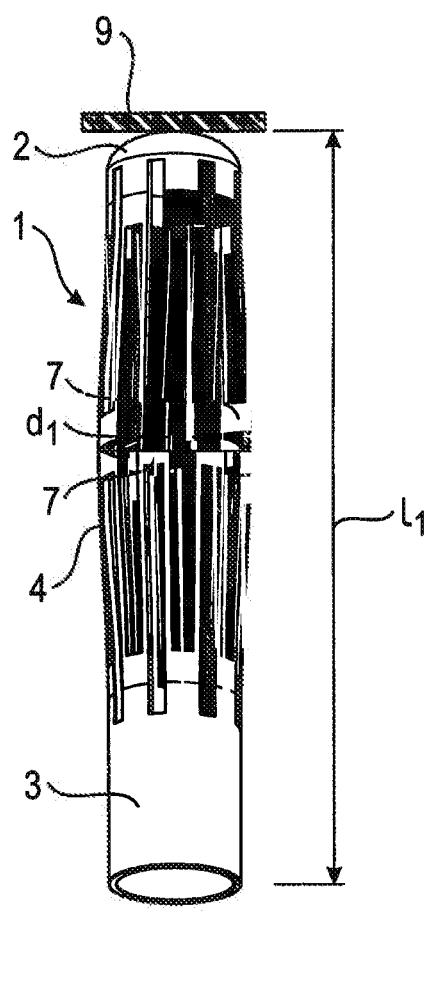
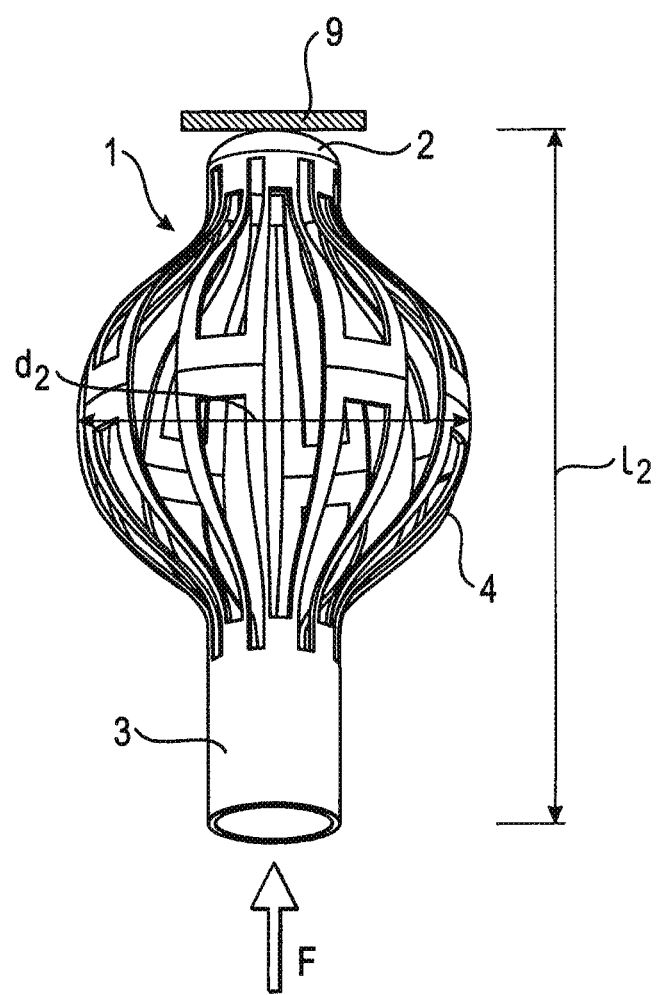

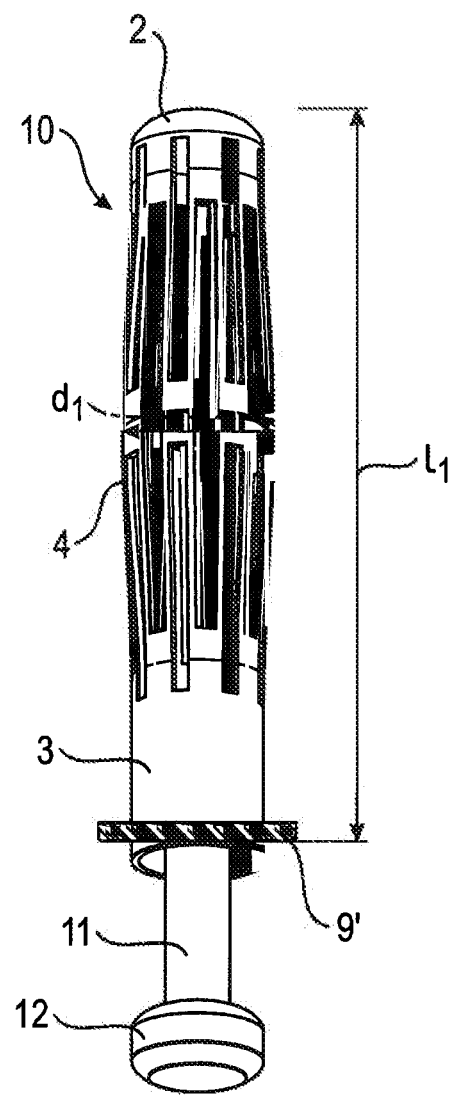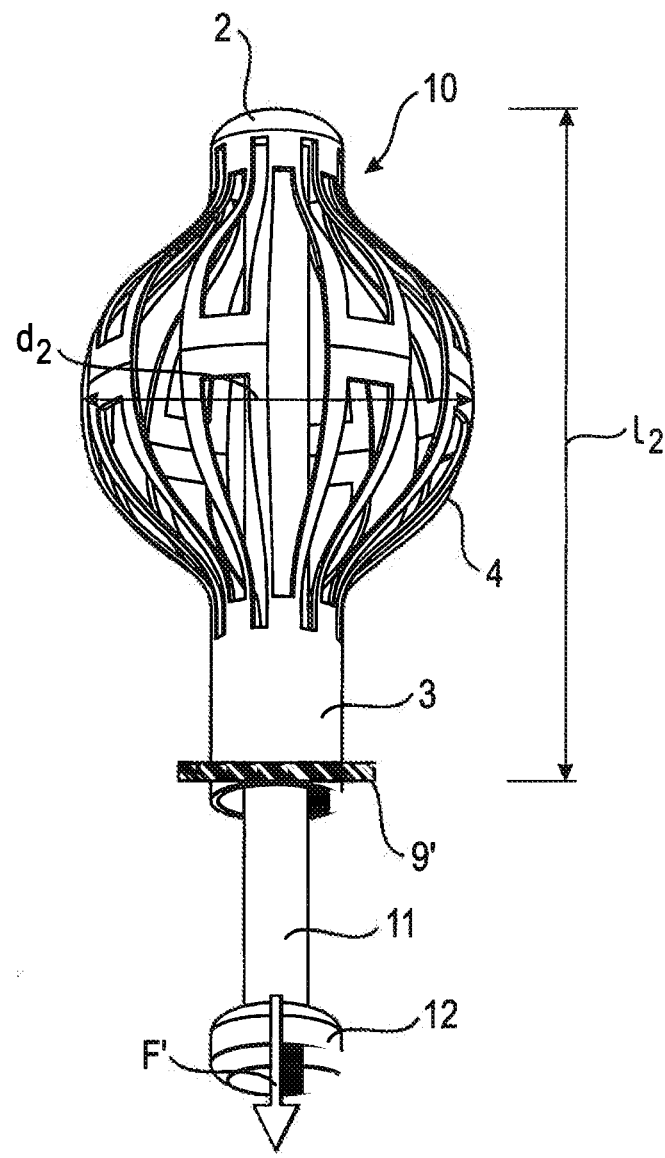

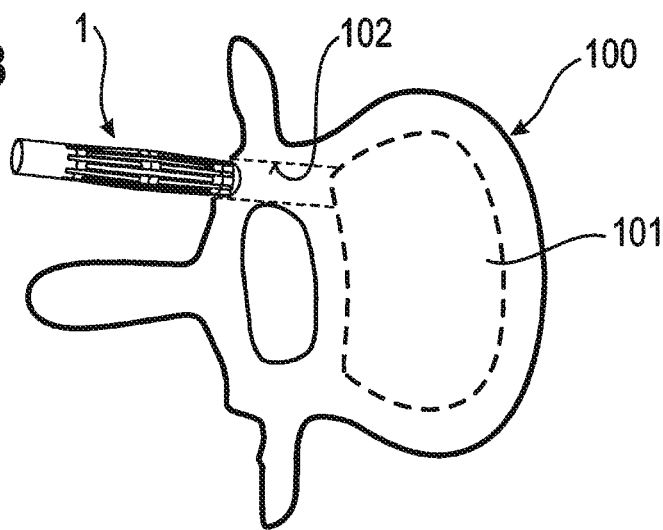
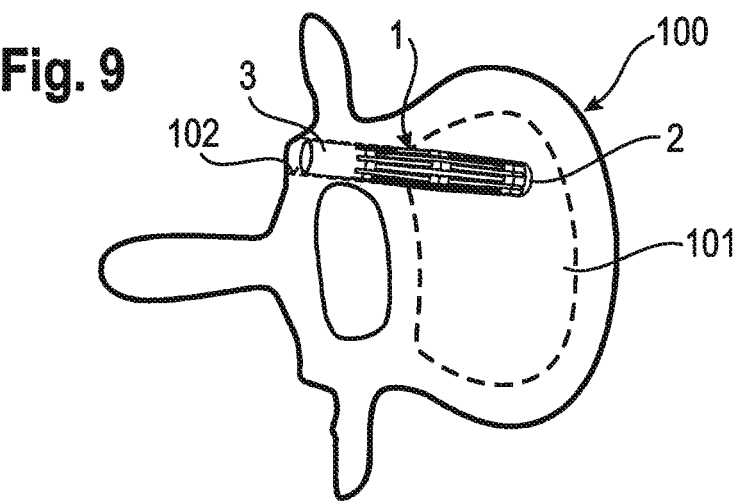
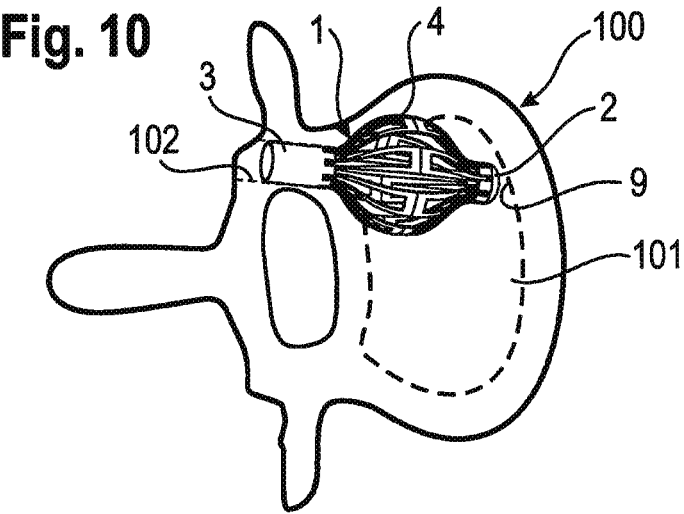

US 8,784,491 B2

IMPLANT FOR STABILIZING VERTEBRAE OR BONES

CROSS-REFERENCE TO RELATED APPLICATION(S)

The present application claims the benefit of U.S. Provisional Patent Application Ser. No. 61/017,523, filed Dec. 28, 2007, the contents of which are hereby incorporated by reference in their entirety, and claims priority from European Patent Application EP 07 025 214.3, filed Dec. 28, 2007, the contents of which are hereby incorporated by reference in their entirety.

BACKGROUND

The invention relates to an implant for stabilizing vertebrae or bones. In particular, the invention relates to an implant for stabilizing an osteoporotic vertebral body.

A known method for the treatment of vertebral body fractures is the so called vertebroplasty. Bone cement of low viscosity is injected with high pressure directly into the fracture site of the vertebral body. There is a risk that a portion of the bone cement exits the vertebral body and flows into the surrounding area. This may cause discomfort or pain since the bone cement can press onto nerves or the spinal cord. Also, the vascular structure beyond the vertebral end plates can be damaged.

Another method for the treatment of vertebral body fractures is the so-called kyphoplasty. The method consists in first inserting a canula into the broken vertebral body. Then a balloon catheter is inserted into the vertebral body. The balloon is expanded by means of injecting a fluid under X-ray monitoring thereby creating a cavity defined by the balloon catheter volume. Thereafter, the fluid is discharged and the balloon is removed. In a next step bone cement is injected into the cavity. The bone cement can be a bone cement with high viscosity compared to that used in vertebroplasty. Although the risk of bone cement escaping into the surrounding is lower than in vertebroplasty, the risk is still not negligible. Also due to the size of the cavity the amount of bone cement used is substantial.

Both of these methods can also be applied to weak and partly collapsed osteoporotic vertebrae.

A problem which is common to vertebroplasty and kyphoplasty is that the vertebral bodies become completely stiffened which enhances the likelihood of a fracture of the neighbouring vertebral bodies due to overloading.

Based on the foregoing, there is a need to provide an implant for the stabilization of vertebrae or bones which overcomes the above mentioned problems.

SUMMARY OF THE INVENTION

The implant according to the invention can be used without bone cement. Therefore, there is no risk of damaging the vascular structure beyond the vertebral end plate. The long-term outcome of the treatment is improved. The implant forms an internal flexible support of the end plate which reduces the risk of a fracture of neighbouring vertebrae.

Further features and advantages of the invention will become apparent from the detailed description of embodiments referring to the accompanying drawings.

BRIEF DESCRIPTION OF THE DRAWINGS

FIG. 4 shows a perspective view of the implant of FIG. 1 abutting against a stop before it is expanded.

FIG. 5 shows the step of expanding the implant of FIG. 4.

FIG. 6 shows a second embodiment of the implant abutting against a stop before it is expanded.

FIG. 7 shows the implant of FIG. 6 when it is expanded.

FIGS. 8 to 11 show steps of inserting the implant into the vertebral body and expanding it.

DETAILED DESCRIPTION OF THE INVENTION

Figure 1:
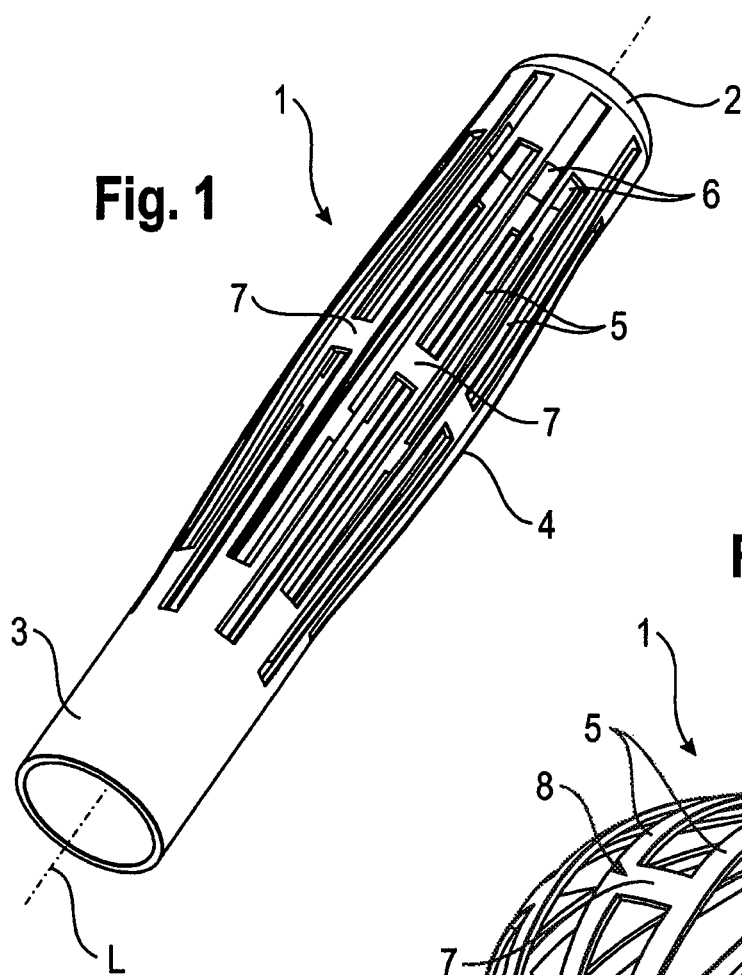
FIG. 1 shows a perspective view of an embodiment of the implant in a state in which it can be inserted.

A first embodiment of the implant is described with reference to FIGS. 1 and 2. The implant 1 is tubular with a longitudinal axis L and includes a first end section 2 and a second end section 3 and an intermediate section 4. The intermediate section 4 includes of a plurality of longitudinal strips 5 extending from the first end section 2 to the second end section 3. There are gaps or slots 6 between the longitudinal strips 5 which also extend from the first end section 2 to the second end section 3. Pairs of longitudinal strips 5 are connected to each other approximately at their center when seen in the longitudinal direction via a transverse strip 7, respectively. Hence, two longitudinal strips 5 and the connecting transverse strip 7 form a strip unit 8. As can be seen, every second of the slots 6 extends further into the tubular end sections 2 and 3. The strips 5 provide flexibility to the intermediate section 4 in such a manner that as shown in FIG. 2, the intermediate section 4 can be expanded like a balloon by outward bending of the strip units 8 thereby widening the slots 6 between the strip units 8. The dimension of the implant is such that it can be inserted through a hole formed in the pedicle of a vertebra into the vertical body. In particular, the length of the intermediate section 4 is selected such that in an expanded state as shown in FIG. 2 the intermediate section 4 can be accommodated in a vertebral body. The number of longitudinal and transverse strips, their shape, their distance and their thickness are selected so as to provide the desired elasticity and desired dimensions to the expanded implant.

The implant can be made of biocompatible material, in particular of a biocompatible metal such as titanium or a biocompatible plastics such as PEEK (polyaryletheretherketone). Particularly suitable are materials such as shape memory alloys exhibiting shape memory properties and/or superelasticity. One example of a suitable material is a nickel titanium alloy such as nitinol.

The implant can be made from a tube where the intermediate section 4 is produced by cutting slots into the tube to create the strips, for example by means of laser cutting.

Figure 2:
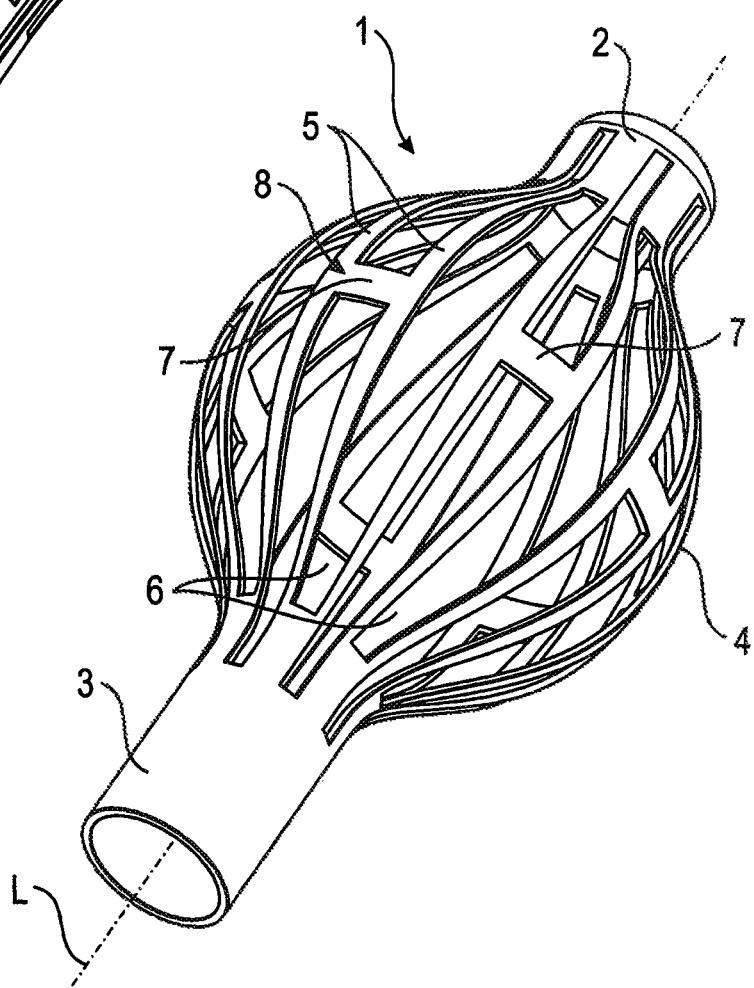
FIG. 2 shows a perspective view of the implant of FIG. 1 in an expanded state.

As can be seen in FIGS. 1 and 2, the first end section 2 is shorter than the second end section 3 and the first end section 2 can have a closed end (not shown). The first end section 2 is used as the proximal end section which is introduced first into the vertebral body whereas the second end section 3 can be adapted for engagement with a tool or with further implant parts.

Figure 3:
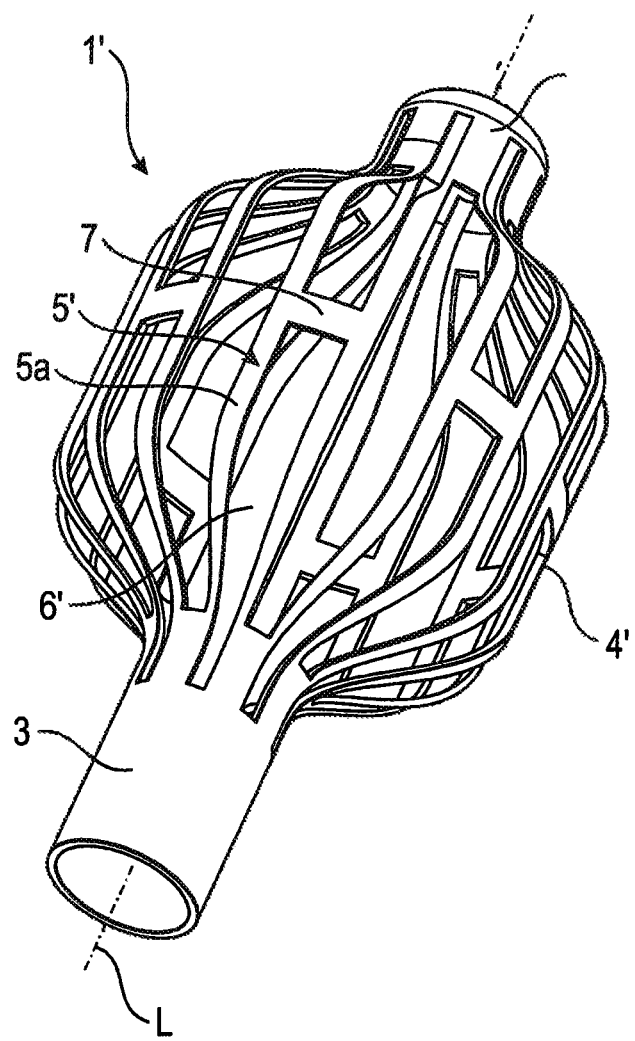
FIG. 3 shows a modified embodiment of the implant in an expanded state.

FIG. 3 shows a perspective view of a modified embodiment 1' of the implant which differs from the implant 1 shown in FIGS. 1 and 2 by the shape of the expanded intermediate section 4'. The other parts are identical and therefore, the description thereof is not repeated. While the intermediate section 4 shown in FIG. 2 has approximately a spherical or ellipsoidal shape, the intermediate section 4' of the implant 1' in FIG. 3 comprises flat portions 5a' of strips 5' extending in parallel to the longitudinal axis L. The strips 5' are shaped in such a way that when expanding the intermediate section 4' it forms an approximately polygonal shape which tapers towards the first end section 2 and to the second end section 3.

It should be noted that any desired shape of the expanded intermediate section 4 can be achieved by designing the pattern of longitudinal and transverse strips in a suitable manner. For example, it is possible to design the intermediate section 4 as a pattern of wires extending from the first end section 2 to the second end section 3 and being connected by welding or by intermediate transverse wires in an open mesh-like manner. The flexibility is generated by providing gaps which allow expansion of the intermediate section 4 in a radial direction when the implant is compressed in an axial direction. The intermediate section 4 can also be pre-expanded to some extent. Due to its flexibility, the pre-expanded intermediate section is compressible in a radial direction.

The function of the implant is explained with reference to FIGS. 4 and 5. The implant 1 shown in FIGS. 4 and 5 has two adjacent transverse strips 7 which form one broad transverse strip. However, as described above, any shape of the strips and pattern of the transverse and longitudinal strips can be achieved by a specific shape and specific dimensions of the strips. FIG. 4 shows the implant 1 with the intermediate section 4 in a non-expanded state. The implant 1 has a length $l_1$ between the outermost end of the first end section 2 and the outermost end of the second end section 3 and a diameter $d_1$ at the center of the intermediate portion 4. The implant 1 abuts against a stop or an abutment 9 with the first end section 2. The abutment is, for example, an inner wall portion of the vertebral body. When a force F is exerted in an axial direction to press the implant 1 with the first end section 2 against the abutment 9 as shown in FIG. 5, the intermediate section 4 expands like a balloon and assumes a shape which in this embodiment is roughly spherical or ellipsoidal. In this expanded state the implant has a length $l_2$ which is smaller than $l_1$ and a diameter $d_2$ which is larger than diameter $d_1$ in the non-expanded state. Hence, the intermediate section 4 is flexible in such a manner that it is expandable in a radial direction when a force acts in an axial direction which reduces the distance between the first end section 2, and the second end section 3.

A second embodiment 10 of the implant is shown in FIGS. 6 and 7. Portions which are identical to the previous embodiments are indicated with the same reference numerals and the description thereof is not repeated. The implant 10 differs from the implant according to the previous embodiments in that it includes a tension element 11 which is provided inside the tubular implant and which is connected to one end, in the embodiment shown it is connected to the first end section 2. It extends through the intermediate section 4 and the second end section 3 to the outside. At its end opposite to the first end section 2 the tension element 11 includes an end portion 12 which can be shaped so as to facilitate gripping. The diameter of the end portion 12 can be larger than the diameter of the second end section 3 so that the end portion 12 forms a stop with respect to the second end section 3. The tension element 11 can be, for example, a rod or a wire. It can be made of any biocompatible material. The function of the implant 10 according to the second embodiment is different from that of the previous embodiments in that the stop 9' has to be provided at the second end portion 3. When a force F' is applied in axial direction pulling the tension element 11 away from stop 9', the implant 10 is compressed in an axial direction from a length $l_1$ to a smaller length $l_2$ while the intermediate section 4 expands from a diameter $d_1$ to a larger diameter $d_2$.

The second embodiment is useful for such cases where it is not possible to provide a stop at the proximal first end section 2.

Figure 11:
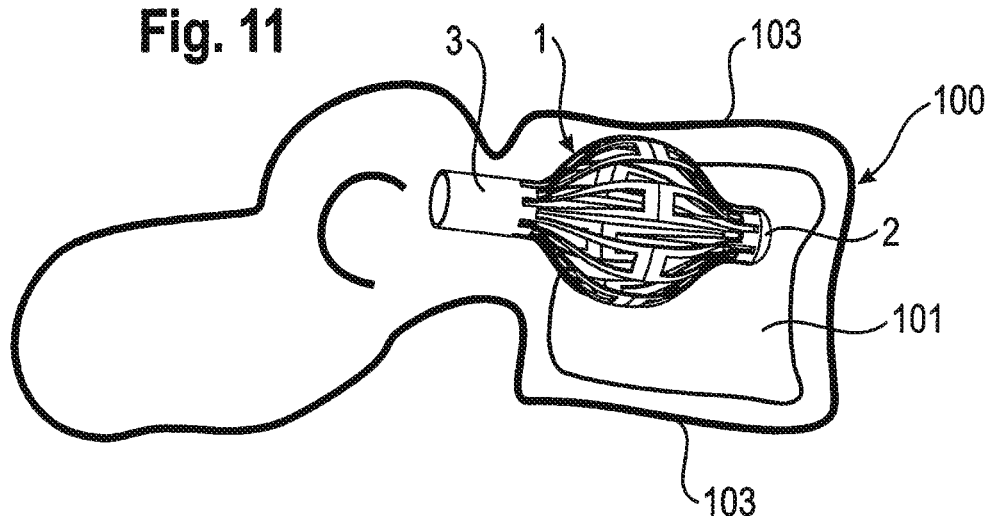

Use of the implant is now explained with reference to FIGS. 8 to 11. FIGS. 8 to 10 show schematic views of a vertebra 100 from the top and FIG. 11 from the side. The vertebral body 101 is damaged (not shown), for example, by osteoporosis or by a fracture. First, as shown in FIG. 8 a hole 102 is prepared in the pedicle of vertebra 100, the hole reaching the damaged inner vertebral body 101. The implant 1 is inserted into the hole and, as shown in FIG. 9, pushed into the vertebral body 101 until the end section 2 abuts against the inner wall, which forms a stop 9 for the implant. When pushing the implant 1 against stop 9 the intermediate section 4 expands into the vertebral body. As can be seen in FIG. 11 the expanded implant which is compressible to some extent in the region of its intermediate section 4 forms a flexible support for the end plate 103 thereby approximating the elastic properties of the vertebral body. By means of this an overstressing of neighbouring vertebrae which can result in a fracture of neighbouring vertebrae can be reduced.

The implant 1 can be held in place by closing the hole, for example with a closure screw (not shown) which can be screwed into the hole 102 and which presses onto the second end section 3.

As shown in FIG. 10, the intermediate section 4 is fully expanded. However, the intermediate section can also be expanded only partially. This may be the case when the intermediate section is not fully introduced into the vertebral body and a part of the intermediate section 4 is constrained by the surrounding wall of the hole 102.

Figure 12:
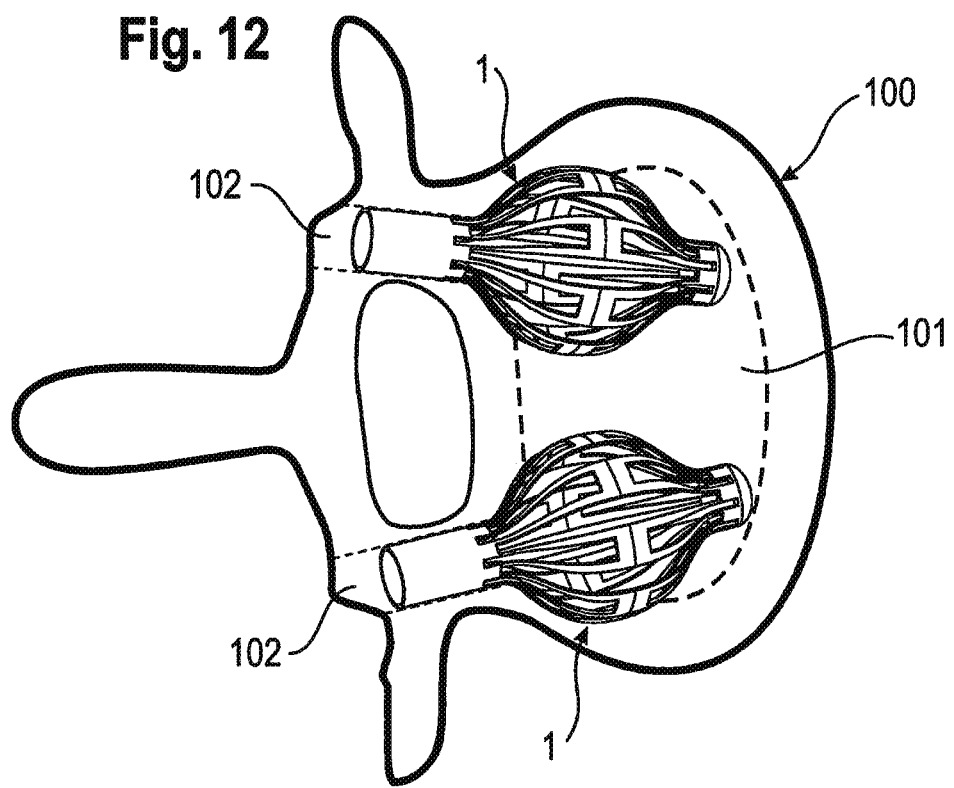
FIG. 12 shows two implants inserted and expanded.

As shown in FIG. 12 two implants can be used in a single vertebra which are inserted from the left and the right pedicle, respectively. This provides a more symmetric stabilization. It remains the choice of the surgeon to use one or two implants according to the clinical situation.

Figure 13:
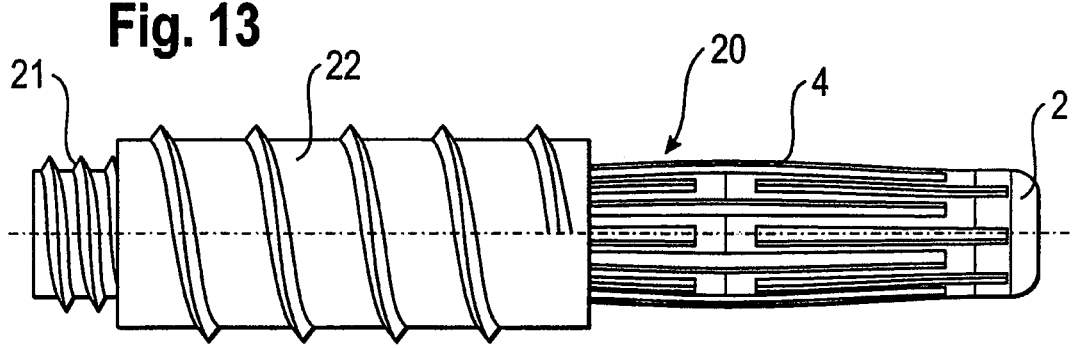
FIG. 13 shows a side view of a third embodiment of the implant used together with a pedicle bushing.
Figure 14:
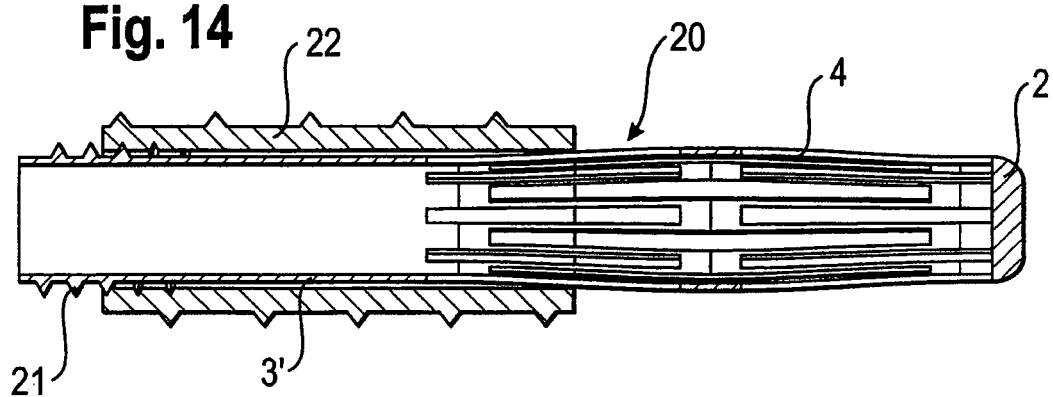
FIG. 14 shows the implant of FIG. 13 in a partially sectional view.
Figure 15:
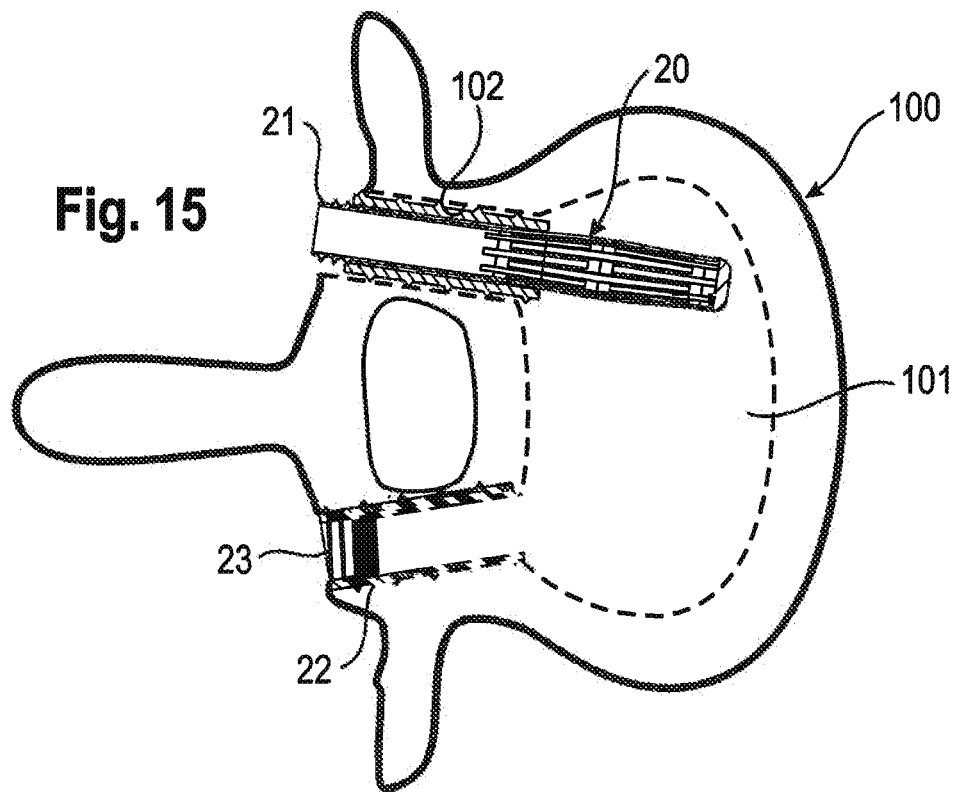
FIG. 15 shows a schematic sectional view of a vertebral body with a pedicle bushing and an implant according to FIGS. 13 and 14.

FIGS. 13 to 15 show a third embodiment of the implant. The implant 20 differs from the previously described embodiments by the structure of the second end section. Other parts of the implant 20 which are identical to those of the previous embodiments are designated with the same reference numerals and the description thereof is not repeated. The implant 20 comprises an end section 3' which is prolonged compared to the end section 3 of the implant of the previous embodiments. The second end section 3' includes a portion 21 with an outer thread which is preferably provided at the end facing away from the intermediate section 4. The outer thread can be a metric thread. The length of the second end section is such that in the inserted state shown in FIG. 15 the second end section 3' extends through the pedicle area.

The implant further comprises a bushing 22 provided with a bone thread for engaging the inner wall of the hole 102. Instead of a bone thread, the outer diameter of the bushing 22 can be slightly oversized with respect to the diameter of the hole 102 such that a press-fit connection is formed between the pedicle hole and the bushing or it can be roughened so that it is held in the hole 102 by friction. The bushing 22 further includes at one end a portion 23 with an inner thread which cooperates with the outer thread of the portion 21 of the second end section 3' of the implant. The length of the bushing is approximately the same as that of the pedicle hole 102. The bushing is oriented in the pedicle hole 102 in such a manner that the portion 23 with the inner thread is directed away from the center of the vertebral body 101.

In use, first, the bushing 22 is inserted into the hole 102 then the implant 20 is guided through the bushing 22 until the threaded portions 21 and 23 of the implant and the bushing, respectively, come into engagement. By further screwing the implant into the bushing until the first end section abuts against the inner wall of the vertebral body the intermediate section 4 is expanded to fill out a portion of the vertebral body. The expanded implant forms a flexible support which stabilizes the vertebral body without the necessity of using bone cement.

Also with respect to this embodiment modifications are possible. The second end section 3' can be made of two pieces wherein the portion having the outer thread is made as a separate piece which is connectable to the implant. The intermediate section 4 can be rotatably fixed to the second end section 3' in such a way that by screwing in the second end section 3' only an axial force is generated with respect to the intermediate section, i.e. the intermediate section 4 does not rotate while advancing into the vertebral body. The end sections need not to be tubular and they can have any other cross section instead of a circular cross section. They can also be curved instead of being linear.

Other means for connecting the implant and the bushing are also conceivable, for example, a press-fit connection.

Figure 16:
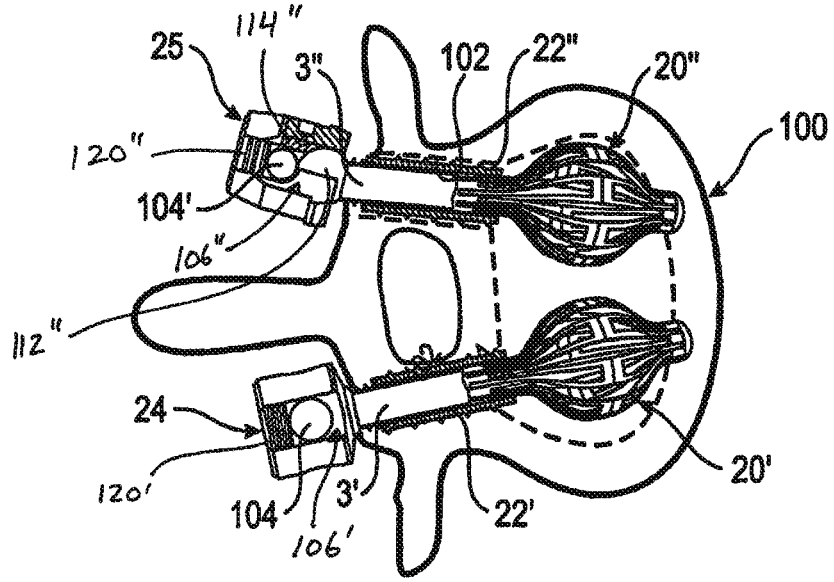
FIG. 16 shows an example of a further application of the implant.

It is also possible to connect the implant to further implant parts such as screw heads which connect spinal rods or other parts to the vertebrae. FIG. 16 shows a schematic top view of the vertebra 100 with two implants 20' and 20" and corresponding bushings 22', 22". One implant 20' includes a receiving part 24' having a recess 106'. The second end section 3' is fixedly or monoaxially connected to the receiving part 24. The receiving part 24 receives a spinal rod 104 in the recess 106'. The rod 104 is then secured by a screw 120'. The other implant 20" includes a receiving part 24" having a recess 106". The second end 3" includes a spherical shaped head 112" which is pivotally received in the recess 106" to provide a polyaxial connection. The implant 20" may include one or more screws 120" (only one shown in FIG. 16) and one or more pressure elements 114" (only one shown in FIG. 16) for securing the rod 104 in the recess 106" and fixing the head 112" to the receiving part 24".

Figure 17:
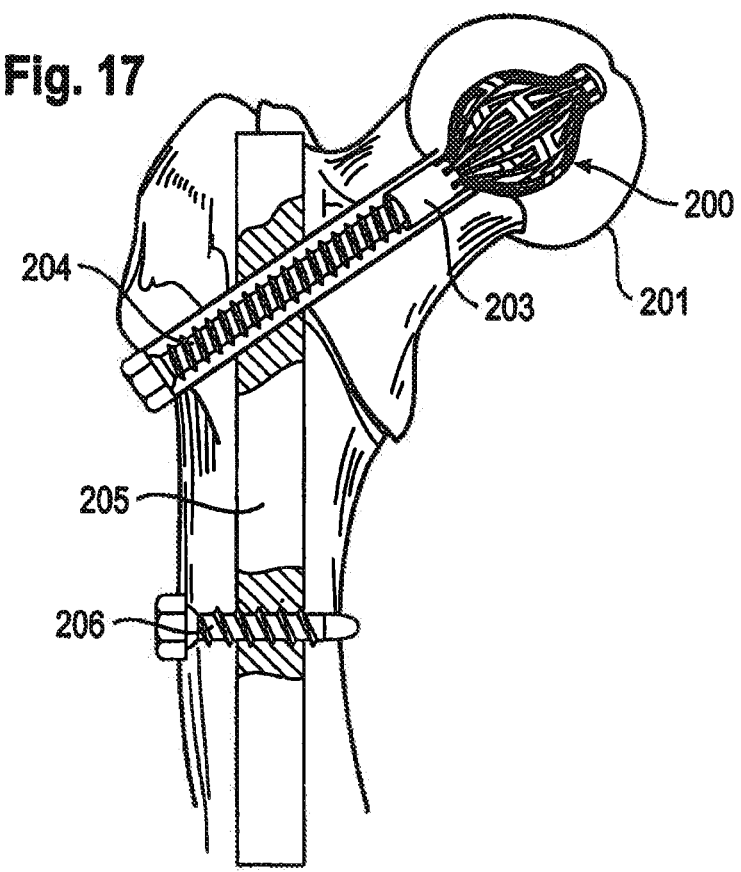
FIG. 17 shows an example of a still further application of the implant.

An additional clinical use of the implants may be the support of weak or fractured bone structures in long bones like the femoral head section, the tibia plateau and other bone areas. FIG. 17 shows the application of the implant 200 to support the femoral head 201. The second end section 203 of the implant 200 is connected to a screw 204 made from biocompatible material, which itself can be connected to a marrow nail 205. At the connection area, the inner diameter of the implant 200 has threads that correspond with the threads on the screw 204. Accordingly, the screw 204 functions as a tensioning screw, such that turning the screw 204 moves one end of the implant relative to the other end. In application, a bore is formed in the bone. The screw 204 and implant 200 are inserted into the bore until the head of the screw 204 abuts on the bone. Thereafter, turning the screw expands the implant 200 at the implantation site. Alternatively, the screw 204 can be used with a bushing 22 as shown in FIG. 13, such that the implant 200 and the screw 204 are guided through the bushing 22. The marrow nail 205 may have an opening, through which the screw 204 can extend. Accordingly, besides having the function of expanding the implant 200, the screw 204 may serve the function of fixing the marrow nail 205 in a vertical direction. Further screws 206 can be provided as usual by which the marrow nail 205 can be fixed.

While a particular form of the disclosure has been illustrated and described, it will be apparent that various modifications can be made without departing from the spirit and scope of the disclosure. Accordingly, it is not intended that the disclosure be limited, except as by the appended claims.

What is claimed is:

1. An implant assembly for use in stabilizing vertebral bodies or bones, comprising:
   a bushing attachable to a bone or vertebrae, the bushing having a bore;
   an implant comprising:
   a first end;
   a second end;
   a flexible tubular section between the first end and the second end having a longitudinal axis extending from the first end to the second end;
   wherein the tubular section is movable between a first position inside the bore of the bushing wherein the first end and the second end are spaced apart and a second position outside the bore of the bushing wherein the first end and the second end are closer together than in the first position and the tubular section is expanded in a radial direction relative to the first position; and
   wherein the bushing or the implant comprises an engagement structure comprising a protruding portion configured to cooperate with the other one of the bushing or the implant to hold a position of the implant relative to the bushing along the longitudinal axis.

2. The implant assembly according to claim 1, wherein the tubular section is formed of strips extending in a direction from the first end to the second end and wherein the strips are connected at their ends, respectively, to the first end and the second end.

3. The implant assembly according to claim 1, wherein the tubular section comprises longitudinal slots in a wall of the tubular section.

4. The implant assembly according to claim 1, wherein the tubular section has an open mesh-like structure.

5. The implant assembly according to claim 1, wherein at least the tubular section is made of a shape memory alloy exhibiting superelasticity.

6. The implant assembly according to claim 1, further comprising a tension element, wherein actuation of the tension element shortens a length of the tubular section.

7. The implant assembly according to claim 1, wherein at least one of the first end and the second end is tubular.

8. The implant assembly according to claim 1, wherein at least one of the first end or the second end of the implant comprises the engagement structure.

9. The implant assembly according to claim 1, wherein the bushing comprises the engagement structure.

10. The implant assembly according to claim 1, wherein the engagement structure comprises threads on the bushing or the implant configured to cooperate with corresponding threads on the other one of the bushing or the implant.

11. The implant assembly according claim 1, wherein the bushing comprises an outer thread.

12. The implant assembly according to claim 11, wherein the outer thread is a bone thread configured to attach the bushing to a bone or vertebrae.

13. The implant assembly according to claim 1, wherein in the first position an outer diameter of the tubular section is less than a diameter of the bore of the bushing, and wherein in the second position the tubular section is expanded in a radial direction to an outer diameter greater than the bore of the bushing.

14. The implant assembly according to claim 1, wherein the implant further comprises a rigid section attached to the flexible tubular section, wherein the rigid section is located in the bore of the bushing in the second position.

15. An implant assembly for use in stabilizing vertebral bodies or bones, comprising:
    a bushing attachable to a bone or vertebrae, the bushing having a bore;
    an implant comprising:
        a first end and a second end;
        a receiver at the second end including a recess configured to receive a rod;
        a flexible tubular section between the first end and the second end having a longitudinal axis extending from the first end to the second end;
        a head between the flexible tubular section and the receiver, the head connected to the receiver;
    wherein the tubular section is movable between a first position inside the bore of the bushing wherein the first end and the second end are spaced apart and a second position outside the bore of the bushing wherein the first end and the second end are closer together than in the first position and the tubular section is expanded in a radial direction relative to the first position.

16. The implant assembly according to claim 15, wherein the tubular section is formed of strips extending in a direction from the first end to the second end and wherein the strips are connected at their ends, respectively, to the first end and the second end.

17. The implant assembly according to claim 15, wherein the tubular section comprises longitudinal slots in a wall of the tubular section.

18. The implant assembly according to claim 15, wherein the tubular section has an open mesh-like structure.

19. The implant assembly according to claim 15, wherein at least the tubular section is made of a shape memory alloy exhibiting superelasticity.

20. The implant assembly according to claim 15, wherein the bushing comprises an engagement structure for engagement with the engagement structure of the first end or the second end.

21. The implant assembly according to claim 20, wherein the engagement structures of the implant and the bushing comprise threads.

22. The implant assembly according to claim 15, wherein the bushing comprises an outer thread.

23. The implant assembly according to claim 15, wherein in the first position an outer diameter of the tubular section is less than a diameter of the bore of the bushing, and wherein in the second position the tubular section is expanded in a radial direction to an outer diameter greater than the bore of the bushing.

24. The implant assembly according to claim 15, wherein the implant further comprises a rigid section attached to the flexible tubular section, wherein the rigid section is located in the bore of the bushing in the second position.

25. The implant assembly according to claim 15, wherein the head is monoaxially connected to the receiver.

26. The implant assembly according to claim 15, wherein the head is polyaxially connected to the receiver.

27. A method of attaching an implant assembly to a vertebral body or a bone to stabilize the vertebral body or bone, the implant assembly comprising a bushing attachable to a bone or vertebrae, the bushing having a bore, an implant comprising a first end, a second end, a flexible tubular section between the first end and the second end having a longitudinal axis extending from the first end to the second end, wherein the tubular section is movable between a first position inside the bore of the bushing wherein the first end and the second end are spaced apart and a second position outside the bore of the bushing wherein the first end and the second end are closer together than in the first position and the tubular section is expanded in a radial direction relative to the first position, and wherein the bushing or the implant comprises an engagement structure comprising a protruding portion configured to cooperate with the other one of the bushing or the implant to hold a position of the implant relative to the bushing along the longitudinal axis, the method comprising:
    forming a bore in a bone or vertebrae to an implantation site;
    attaching the bushing in the bore;
    moving the implant through the bushing to the implantation site; and
    expanding the implant at the implantation site.

28. The method according to claim 27, wherein in the first position an outer diameter of the tubular section is less than a diameter of the bore of the bushing, and wherein in the second position the tubular section is expanded in a radial direction to an outer diameter greater than the bore of the bushing.

* * * * *

UNITED STATES PATENT AND TRADEMARK OFFICE
CERTIFICATE OF CORRECTION

PATENT NO. : 8,784,491 B2  
APPLICATION NO. : 12/343232  
DATED : July 22, 2014  
INVENTOR(S) : Lutz Biedermann et al.

Page 1 of 1

It is certified that error appears in the above-identified patent and that said Letters Patent is hereby corrected as shown below:

On the Title Page

Prior Publication Data         Insert -- Related U.S. Application Data

(60) Provisional application No. 61/017,523
filed on December 28, 2007. --

Signed and Sealed this
Thirtieth Day of December, 2014

Michelle K. Lee
*Deputy Director of the United States Patent and Trademark Office*